(12) United States Patent
Matsui

(10) Patent No.: US 8,094,206 B2
(45) Date of Patent: Jan. 10, 2012

(54) ENDOSCOPE PROCESSOR EXECUTING GAMMA CORRECTION ON IMAGE SIGNALS USING GAMMA COEFFICIENTS

(75) Inventor: Go Matsui, Yamagata (JP)

(73) Assignee: Hoya Corporation, Tokyo (JP)

( * ) Notice: Subject to any disclaimer, the term of this patent is extended or adjusted under 35 U.S.C. 154(b) by 667 days.

(21) Appl. No.: 12/265,140

(22) Filed: Nov. 5, 2008

(65) Prior Publication Data

US 2009/0122135 A1    May 14, 2009

(30) Foreign Application Priority Data

Nov. 12, 2007 (JP) .................................. 2007-293113

(51) Int. Cl.
*H04N 5/228* (2006.01)
(52) U.S. Cl. .................................. 348/222.1; 348/229.1
(58) Field of Classification Search ............... 348/222.1, 348/229.1; 345/76, 204; 358/1.9
See application file for complete search history.

(56) References Cited

U.S. PATENT DOCUMENTS

| | | | |
|---|---|---|---|
| 2005/0213128 A1* | 9/2005 | Imai et al. ........................ | 358/1.9 |
| 2007/0040822 A1* | 2/2007 | Koyama et al. .................. | 345/204 |
| 2007/0070214 A1* | 3/2007 | Nakamura .................. | 348/222.1 |
| 2007/0080905 A1* | 4/2007 | Takahara ........................ | 345/76 |
| 2008/0097151 A1 | 4/2008 | Inoue et al. | |
| 2008/0143826 A1 | 6/2008 | Shibasaki | |
| 2008/0198223 A1 | 8/2008 | Iriyama | |
| 2008/0231694 A1 | 9/2008 | Ohtaki | |
| 2008/0255415 A1 | 10/2008 | Iida | |

FOREIGN PATENT DOCUMENTS

JP    2006-187426    7/2006

OTHER PUBLICATIONS

English language Abstract of JP 2006-187426, Jul. 20, 2006.

* cited by examiner

*Primary Examiner* — Le Luu
(74) *Attorney, Agent, or Firm* — Greenblum & Bernstein, P.L.C.

(57) ABSTRACT

An endoscope processor including a light source controller, an imaging device driver, and a gamma-correction block, is provided. The light source controller can order first and second light sources to alternately emit first and second lights, respectively. The imaging device driver orders an imaging device to generate first and second image signals by capturing an optical image of a subject while the firs and the second light are shone on the subject, respectively. The gamma-correction block carries out gamma correction on the first and second image signals using first and second color gamma coefficients, respectively. The first and second color gamma coefficients are predetermined according to the wavelength band of the first and second lights.

8 Claims, 7 Drawing Sheets

ENDOSCOPE PROCESSOR EXECUTING GAMMA CORRECTION ON IMAGE SIGNALS USING GAMMA COEFFICIENTS

BACKGROUND OF THE INVENTION

1. Field of the Invention

The present invention relates to an endoscope processor which carries out signal processing on an image signal generated on the basis of a captured optical image of a subject illuminated by one type of light selected from among different kinds of light and which carries out the signal processing according to the specific kind of light.

2. Description of the Related Art

A fluorescence endoscope system which shines exciting light on tissue and captures an optical autofluorescence image from the tissue is known. In addition, Japanese Unexamined Patent Publication No. 2006-187426 discloses that a white-light image which is an optical image of a subject illuminated by white light and a fluorescence image of a subject illuminated by exciting light are simultaneously displayed on a monitor in such a fluorescence endoscope system.

In prior fluorescence endoscope systems, color gamma correction is carried out on a white-light image signal and a fluorescence image signal, which are generated by photographing either white light or exciting light, respectively are shone on a subject. However, in prior art, because color gamma correction is carried out on both the white-light image signal and the fluorescence image signal using the same color gamma coefficient, there is a troublesome increase in color noise and/or color fading in the displayed images.

SUMMARY OF THE INVENTION

Therefore, an object of the present invention is to provide an endoscope processor that carries out signal processing on image signals of a subject illuminated by different kinds of light so that color noise can be reduced and color fading can be prevented.

According to the present invention, an endoscope processor comprising a light source controller, an imaging device driver, and a gamma-correction block, is provided. The light source controller can order first and second light sources to alternately emit first and second lights, respectively. The wavelength band of the first light differs from that of the second light. The imaging device driver orders an imaging device to generate first and second image signals by capturing an optical image of a subject while the first and the second light are shone on the subject, respectively. The gamma-correction block carries out gamma correction on the first and the second image signals using first and second color gamma coefficients, respectively. The first and the second color gamma coefficients are predetermined according to the wavelength band of the first and the second light.

Further, the gamma-correction block comprises first and second correction blocks. The first and the second correction blocks carry out gamma correction on the first and the second image signals using the first and the second color gamma coefficients, respectively.

Further, the endoscope processor comprises a coefficient memory. The coefficient memory stores the first and the second color gamma coefficients. The gamma-correction block carries out gamma correction on the first image signal using the first color gamma coefficient stored in the coefficient memory when the gamma-correction block receives the first image signal. The gamma-correction block carries out gamma correction on the second image signal using the second color gamma coefficient stored in the coefficient memory when the gamma-correction block receives the second image signal.

According to the present invention, an endoscope system comprising first and second light sources, a light source controller, a light guide, an endoscope, and a gamma-correction block, is provided. The first and the second light sources emit first and second lights, respectively. The wavelength band of the first light differs from that of the second light. The light source controller can order the first and the second light sources to alternately emit the first and the second lights, respectively. The light guide transmits the first and the second lights emitted by the first and the second light sources to a subject, respectively. The endoscope generates first and second image signals by capturing an optical image of the subject while the first and the second light are shone on the subject, respectively. The gamma-correction block carries out gamma correction on the first and the second image signals using first and second color gamma coefficients, respectively. The first and the second color gamma coefficients are predetermined according to a wavelength band of the first and the second lights.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
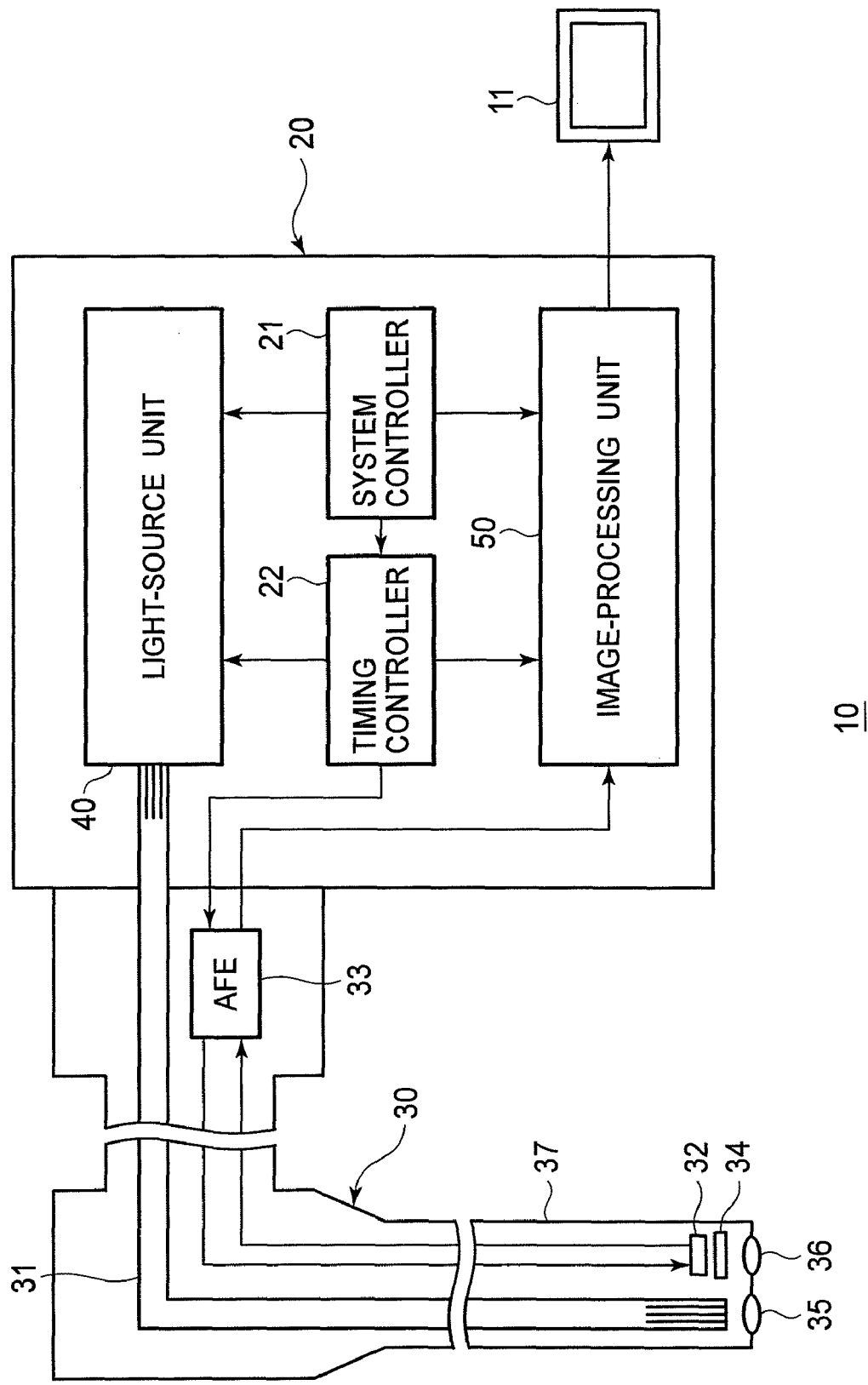
FIG. 1 is a block diagram showing the internal structure of an endoscope system having an endoscope processor of an embodiment of the present invention.

The present invention is described below with reference to the embodiment shown in the drawings.

In FIG. 1, an endoscope system 10 comprises an endoscope processor 20, an electronic endoscope 30, and a monitor 11. The endoscope processor 20 is connected to the electronic endoscope 30 and the monitor 11.

The endoscope processor 20 emits light to illuminate a required subject. An optical image of the illuminated subject is captured by the electronic endoscope 30, and then the electronic endoscope 30 generates an image signal. The image signal is sent to the endoscope processor 20.

The endoscope processor 20 carries out predetermined signal processing on the received image signal, and then a video signal is generated. The video signal is sent to the monitor 11, where an image corresponding to the video signal is displayed.

The endoscope processor 20 comprises a light-source unit 40, an image-processing unit 50 (gamma-correction block), a system controller 21, a timing controller 22 (light source controller), and other components. As described below, the light-source unit 40 emits white light for illuminating a desired subject, and/or exciting light, which makes tissue autofluoresce. In addition, as described in detail below, the image-processing unit 50 carries out predetermined signal processing on the image signal.

The system controller 21 controls the operations of all components of the endoscope processor 20, including the light-source unit 40 and the image-processing unit 50. The timing controller 22 times some operations of the components of the endoscope processor 20.

By connecting the endoscope processor 20 to the electronic endoscope 30, the light-source unit 40 and a light-guide 31 mounted in the electronic endoscope 30 are optically connected. In addition, by connecting the endoscope processor 20 to the electronic endoscope 30, electrical connections are made between the image-processing unit 50 and the imaging device 32 mounted in the electronic endoscope 30, and between the timing controller 22 and the imaging device 32 via the AFE (Analog Front End) 33.

Figure 2:
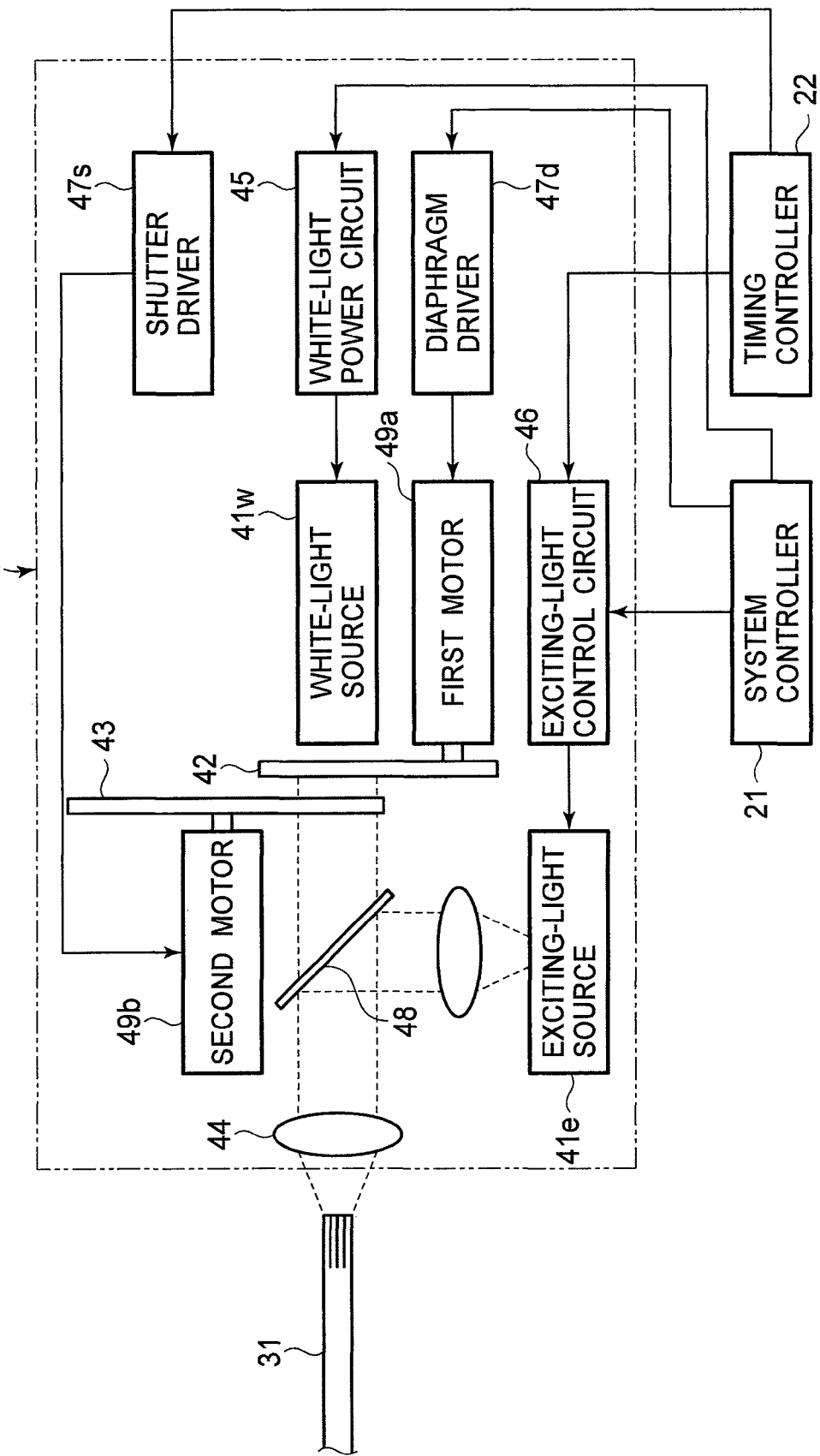
FIG. 2 is a block diagram showing the internal structure of a light-source unit.

As shown in FIG. 2, the light-source unit 40 comprises a white-light source 41w, an exciting-light source 41e, a diaphragm 42, a shutter 43, a condenser lens 44, a white-light power circuit 45, an exciting-light control circuit 46, a shutter driver 47s, a diaphragm driver 47d, and other components.

The white-light source 41 emits white light. The exciting-light source 42 emits exciting light of specified wavelength, such as in the ultraviolet range.

The diaphragm 42, the shutter 43, a dichroic mirror 48, and the condenser lens 44 are mounted between the white-light source 41w and the light guide 31. The white light emitted by the white-light source 41w passes the dichroic mirror 48, is condensed by the condenser lens 44, and is directed to the incident end of the light guide 31. The white-light power circuit 45 supplies the white-light source 41w with power.

The intensity of the white light used to illuminate a subject, is controlled by adjusting the aperture ratio of the diaphragm 42. The aperture ratio of the diaphragm 42 is adjusted by a first motor 49a. The movement of the first motor 49a is controlled by the diaphragm driver 47d. The diaphragm driver 47d is connected to an image-processing unit 50 via a system controller 21.

As described below, the image-processing unit 50 detects the intensity of light received in the captured image of a subject based on the image signal generated by the imaging device. The detected intensity of light is communicated to the diaphragm driver 47d via the system controller 21. The diaphragm driver 47d calculates the necessary degree of adjustment for the first motor 49a based on the intensity of light received.

The shutter 43 is a rotary shutter having an aperture area and a blocking area. The shutter 43 controls the passage of, or blocks the white light. When white light should be allowed to pass, the aperture area is inserted into the optical path of the white light. When white light should be blocked, the blocking area is inserted into the optical path of the white light. The shutter 43 is driven by a second motor 49b. The movement of the second motor 49b is controlled by the shutter driver 47s.

Exciting light emitted by the exciting-light source 41e is reflected by the dichroic mirror 48, condensed by the condenser lens 44, and directed to the incident end of the light guide 31. The exciting-light control circuit 46 switches the exciting-light source 41e between lighting on and off.

The shutter driver 47s and the exciting-light control circuit 46 are connected to the timing controller 22. The white-light control signal, for controlling the aperture time and blockage time of white light by shutter 43 is output from the timing controller 22 to the shutter driver 47s. In addition, the exciting-light control signal for controlling times to switch the exciting-light source 41e between lighting on and off is output from the timing controller 22 to the exciting-light control circuit 46. Both the white-light control signal and the exciting-light control signal are oscillating signals.

When the white-light control signal is in the high state, the shutter driver 47s drives shutter 43 so as to pass the white light. On the other hand, when the white-light control signal is in the low state, the shutter driver 47s drives the shutter 43 so as to block the white light.

When the exciting-light control signal is in the high state, the exciting-light control circuit 46 switches the exciting-light source 41e on. On the other hand, when the exciting-light control signal is in the low state, the exciting-light control circuit 46 switches the exciting-light source 41e off.

The timing controller 22 controls the high and low states of the white-light control signal and the exciting-light control signal so that the high and low states of the white-light control signal inverted with respect to the exciting-light control signal. Accordingly, when the white-light control signal and the exciting-light control signal are in high and low states, respectively, the white light is supplied to the incident end by the light source unit 40. On the other hand, when the white-light control signal and the exciting-light control signal are in low and high states, respectively, the exciting light is supplied to the incident end by the light source unit 40.

The white-light power circuit 45 and the exciting-light control circuit 46 are connected to the system controller 21. The system controller 21 switches the white-light power circuit 45 and the exciting-light control circuit 46 between on and off.

Next, the structure of the electronic endoscope 30 is explained in detail. As shown in FIG. 1, the electronic endoscope 30 comprises the light guide 31, the imaging device 32, the AFE (analog front end) 33, an exciting-light cut-off filter 34, and other components.

The incident end of the light guide 31 is mounted in a connector (not depicted) which connects the electronic endoscope 30 to the endoscope processor 20. And the other end, hereinafter referred to as the exit end, is mounted at the head end of the insertion tube 37 of the electronic endoscope 30. As described above, the white light or the exciting light emitted by the light-source unit 40 arrives at the incident end of the light guide 31. The light is then transmitted to the exit end. The light transmitted to the exit end illuminates a peripheral area near the head end of the insertion tube 37 through a diffuser lens 35.

At the head end of the insertion tube 37, an object lens 36, the exciting-light cut-off filter 34, and the imaging device 32 are also mounted. The exciting-light cut-off filter 34 is arranged between the object lens 36 and the imaging device 32.

An optical image of the subject illuminated by the white light or the exciting light is formed on the light-receiving surface of the imaging device 32 through the object lens 36 and the exciting-light cut-off filter 34.

The exciting-light cut-off filter 34 cuts off the whole band of the exciting light emitted by the exciting-light source 41e. Accordingly, the same light component as the exciting light emitted by the exciting-light source 41e from an optical image of the subject illuminated by the white light or the exciting light is attenuated by the exciting-light cut-off filter 34. The optical image passing through the exciting-light cut-off filter 34 reaches the light-receiving surface of the imaging device 32.

The AFE 33 comprises an imaging device driver (not depicted). The imaging device driver drives the imaging device 32 so that the imaging device 32 can capture an optical image incident on the light-receiving surface during each field period. Field periods are usually 1/60 second in duration. The timing of various operations for driving the imaging device 32 by the imaging device driver is controlled by the timing controller 22.

The imaging device 32 generates an image signal based on the optical image captured by the light-receiving surface. The generated analog image signal is digitized by the AFE 33. The digital image signal is sent to the image-processing unit 50 every field period.

Figure 3:
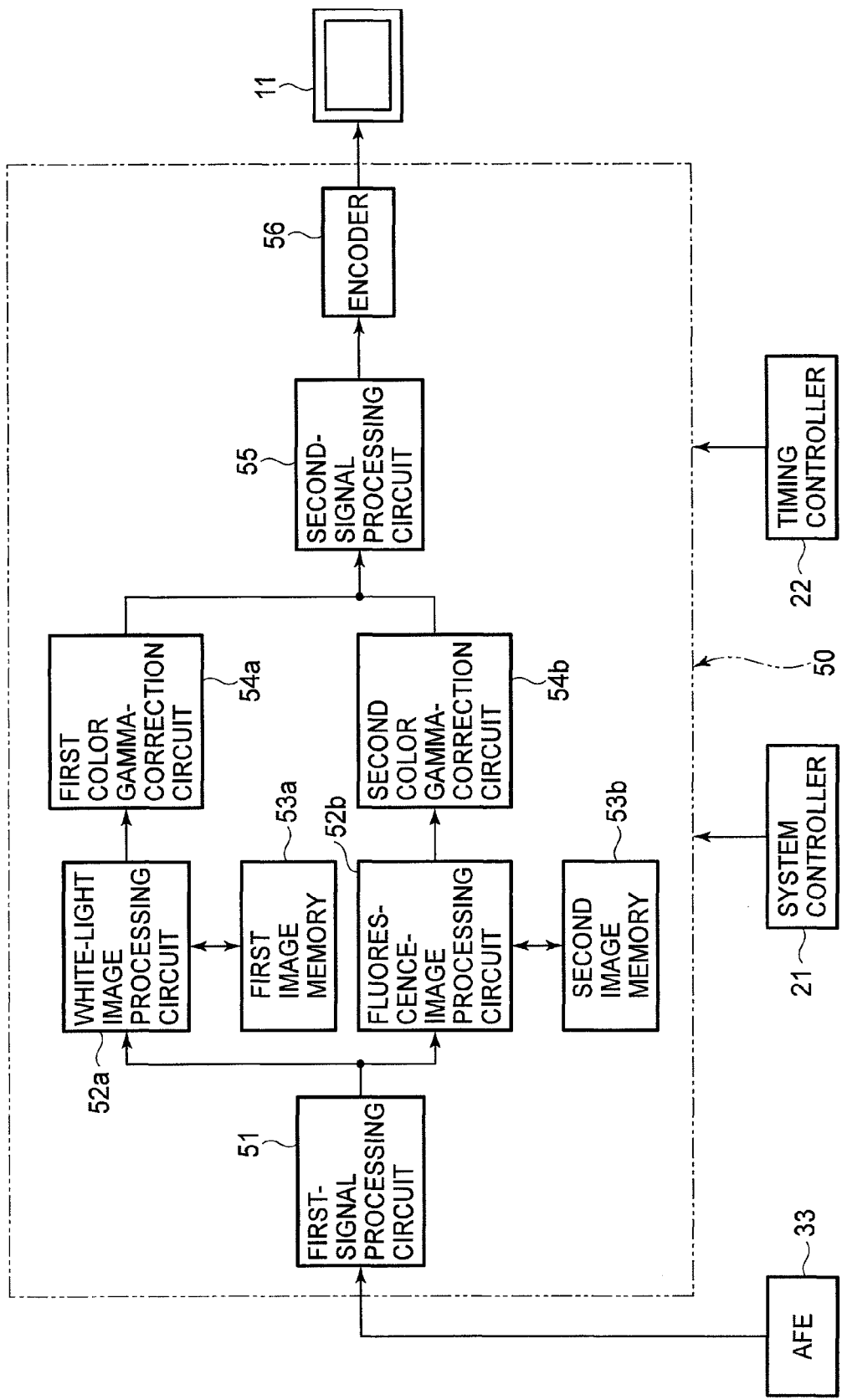
FIG. 3 is a block diagram showing the internal structure of an image-processing unit.

Next, the structure of the image-processing unit 50 is explained using FIG. 3. The image-processing unit 50 comprises a first-signal processing circuit 51, a white-light image processing circuit 52a, a fluorescence-image processing circuit 52b, first and second image memories 53a and 53b, first and second color gamma-correction circuits 54a and 54b (first and second correction blocks), a second-signal processing circuit 55 (image generation block), an encoder 56, and other components.

The image-processing unit 50 is connected to the timing controller 22. The timing controller 22 sends the white light control signal and the exciting-light control signal to the image-processing unit 50. When the white-light control signal is in the high state, the image-processing unit 50 determines that a received image signal is a white-light image signal. On the other hand, when the exciting-light control signal is in the high state, the image-processing unit 50 determines that the received image signal is instead a fluorescence image signal.

The white-light image signal and the fluorescence image signal received by the image-processing unit 50 are input to the first-signal processing circuit 51. The first-signal processing circuit 51 carries out gain-control processing on the white-light image signal and the fluorescence image signal. Through gain-control processing, median luminance value among the whole pixel signals which compose a white-light image signal and a fluorescence image signal is set according to the median value of the digital signal level of the first-signal processing circuit 51. In addition, the first-signal processing circuit 51 carries out predetermined signal processing, such as color interpolation, on the white-light image signal and the fluorescence image signal.

As described above, the average intensity of light of a white-light image is calculated on the basis of the white-light image signal prior to gain-control processing. The calculated average intensity of light is communicated to the diaphragm driver 47d via the system controller 21, and used for calculating the degree of adjustment required for the diaphragm 42.

Once undergoing predetermined signal processing, the white-light image signal and the fluorescence-image signal are sent to the white-light image processing circuit 52a and the fluorescence-image processing circuit 52b, respectively.

The white-light image processing circuit 52a carries out signal processing predetermined for the white-light image on the received white-light image signal. After carrying out the predetermined signal processing, the white-light image processing circuit 52a sends the white-light image signal to the first image memory 53a and the first color gamma-correction circuit 54a. The white-light image signal is stored in the first image memory 53a.

The fluorescence-image processing circuit 52b carries out signal processing predetermined for a fluorescence image on the received fluorescence image signal. After carrying out the predetermined signal processing, the fluorescence-image processing circuit 52b sends the fluorescence image signal to the second image memory 53b and the second color gamma-correction circuit 54b. The fluorescence image signal is stored in the second image memory 53b.

Figure 4:
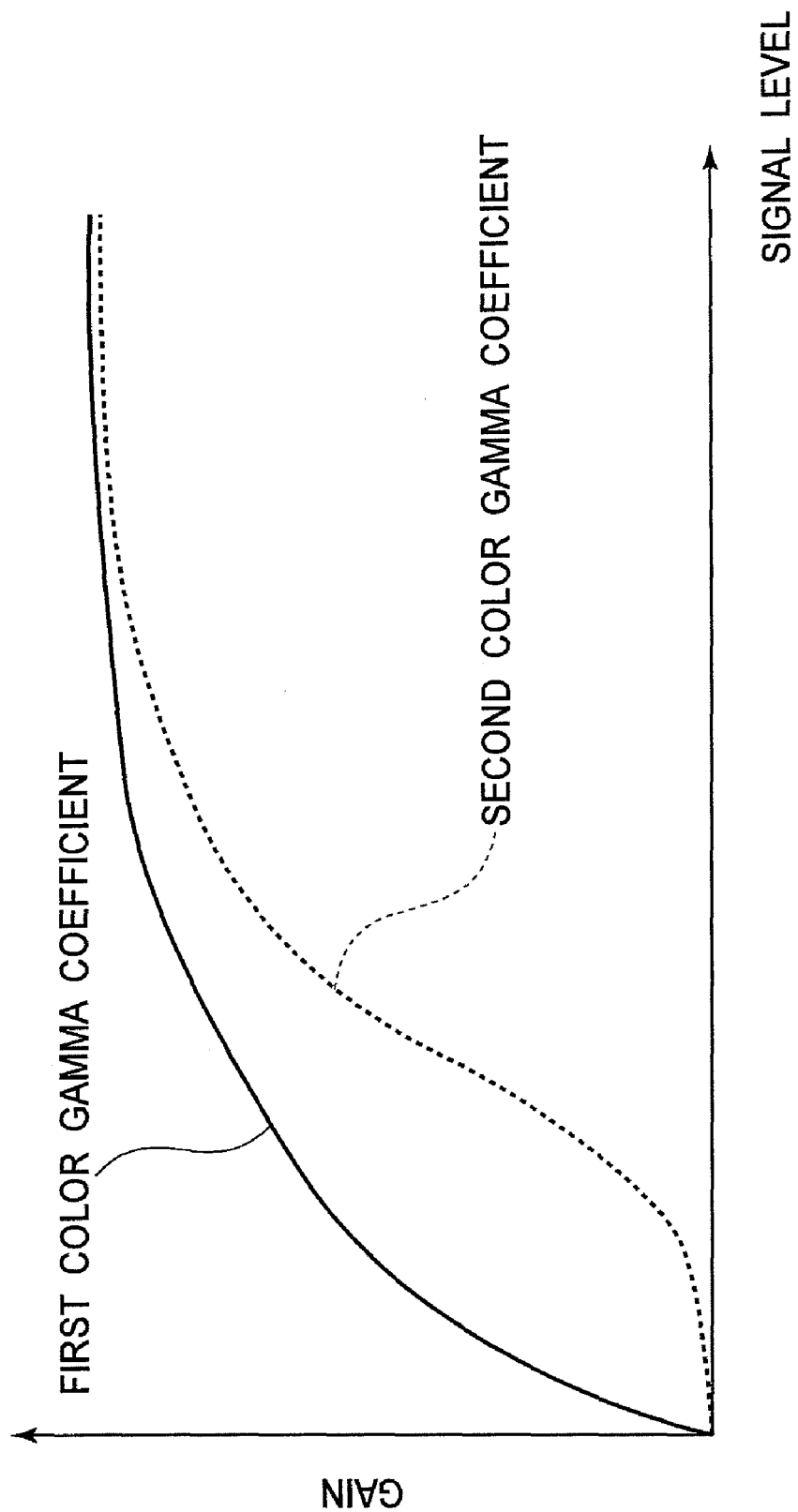
FIG. 4 is a graph showing the first and the second color gamma coefficients according to signal level.

The first color gamma-correction circuit 54a carries out color gamma correction on the received white-light image signal using a first color gamma coefficient. As shown in FIG. 4, the first color gamma coefficient is a gain which varies according to the signal level of each pixel signal, and is predetermined so that color response will approach veridicality for all pixels across the entire luminance range.

The second color gamma-correction circuit 54b carries out color gamma correction on the received fluorescence image signal using a second color gamma coefficient. As shown in FIG. 4, the second color gamma coefficient is a gain which varies according to the level of each pixel signal, and is predetermined so that the second gamma coefficient is lower than the first gamma coefficient especially at the low end of the signal range.

Once color gamma-corrected, the white-light image signal and/or the fluorescence image signal are sent to the second-signal processing circuit 55. The second-signal processing circuit 55 carries out plural image display processing operations as required. In addition, the second-signal processing circuit 55 carries out predetermined signal processing, such as clamping, blanking, and so on, and D/A conversion. A video signal generated based on the image signal converted into analog signal is encoded by the encoder 56, and sent to the monitor 11. An image corresponding to the received video signal is displayed on the monitor 11.

Next, an operation of the endoscope system 10 on displaying a captured subject and an image displayed on the monitor 11 are explained. The endoscope system 10 has a white-light image observation mode, a fluorescence image observation mode, and two-image observation mode where an image captured by endoscope is displayed on the monitor 11. One among the white-light image observation mode, the fluorescence observation mode, and the two-image observation mode is selected based on an input operation to an input apparatus (not depicted) of the endoscope 30 and the endoscope processor 20.

Figure 5:
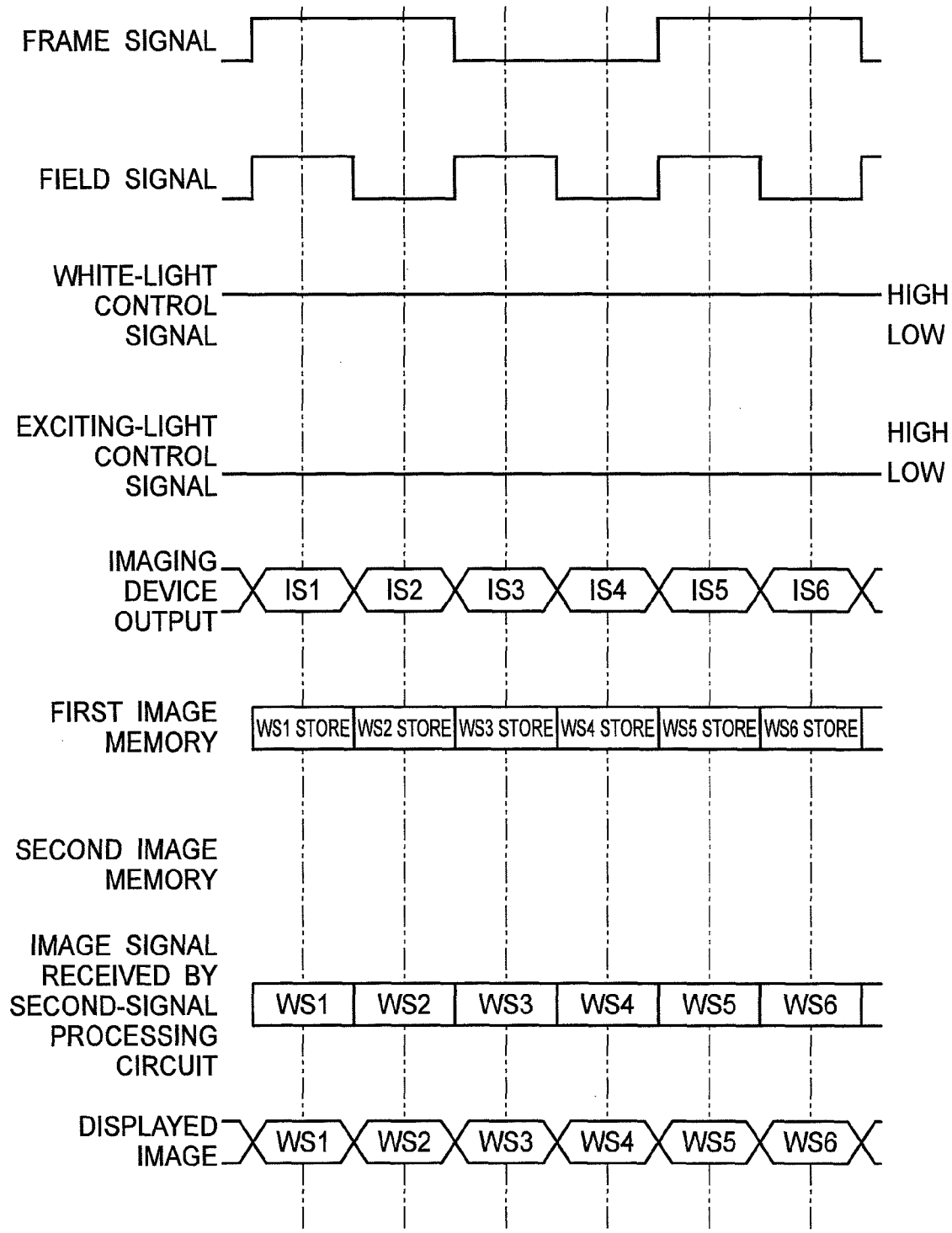
FIG. 5 is a timing chart illustrating the timing used to drive some components in the endoscope system in the white-light image observation mode.

When the white-light image observation mode is selected, the white-light control signal in the high state and the exciting-light control signal in the low state are sent to the shutter driver 47s and the exciting-light control circuit 46 from the timing controller 22, respectively (see the columns of "white-light control signal" and "exciting-light control signal" in FIG. 5).

Accordingly, the light-source unit 40 supplies only the white light to the light guide 31, and then the white light is shone to a subject. An optical image of the subject illuminated by the white light is captured, whenever the field signal is alternately switched between high and low states, and then an image signal (referred to as IS1, IS2, IS3, IS4, IS5, and IS6 in the row "imaging device output" in FIG. 5) is sequentially generated.

When the white-light image observation mode is selected, the white-light control signal in the high state is sent to the image-processing unit 50 also. As described above, the image-processing unit 50 determines that the image signals received from the AFE 33 every field period are white-light image signals. Accordingly, the received all white-light image signals are sent to the white-light image-processing circuit 52a via the first-signal processing circuit 51.

The white-light image signal is sent to the first image memory 53a and the first color gamma-correction circuit 54a from the white-light image-processing circuit 52a, whenever the white-light image signal is received by the white-light image-processing circuit 52a. As described above, the white-light image signal (referred to as WS1, WS2, WS3, WS4, WS5, and WS6 in the row "first image memory" in FIG. 5) is stored in the first image memory 53a. In addition, the first color gamma-correction circuit 54a carries out color gamma correction on the received white-light image signal.

The white-light image signal (referred to as WS1, WS2, WS3, WS4, WS5, and WS6 in the row "image signal received by second-signal processing circuit" in FIG. 5) is sent to the second-signal processing circuit 55 from the first color gamma-correction circuit 54a. The second-signal processing circuit 55 receives an image signal only from the first color gamma-correction circuit 54a, and then, the second-signal processing circuit 55 generates a video signal based on the received white-light image signal without carrying out plural image display processing. There is displayed a white-light image (referred to as WS1, WS2, WS3, WS4, WS5, and WS6 in the row "displayed image" in FIG. 5) which is an optical image of a subject illuminated by the white light on the monitor 11.

Figure 6:
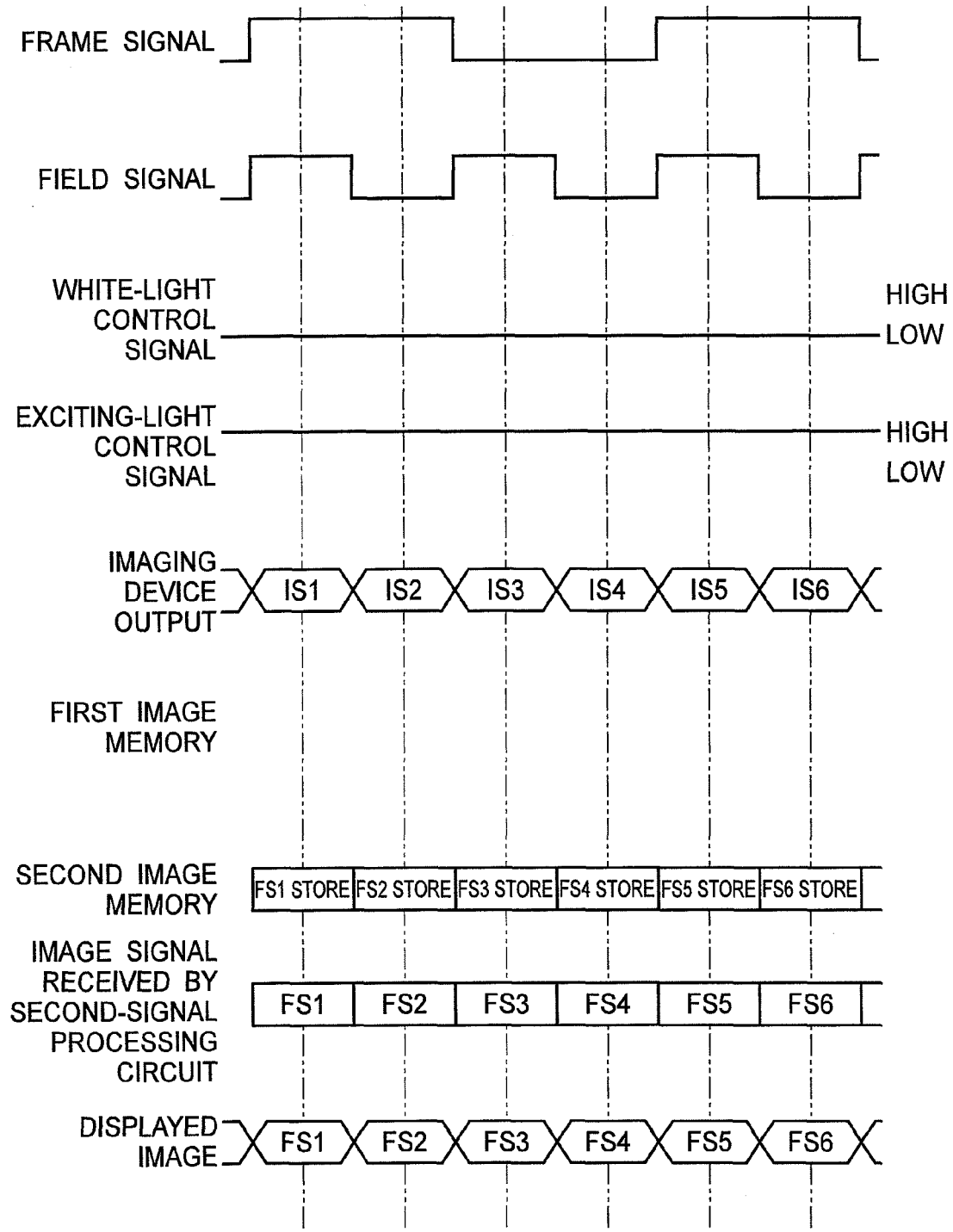
FIG. 6 is a timing chart illustrating the timing used to drive some components in the endoscope system in the fluorescence image observation mode.

When the fluorescence image observation mode is selected, the white-light control signal in the low state and the exciting-light control signal in the high state are sent to the shutter driver 47s and the exciting-light control circuit 46 from the timing controller 22, respectively (see the columns of "white-light control signal" and "exciting-light control signal" in FIG. 6).

Accordingly, the light-source unit 40 supplies only the exciting light to the light guide 31, and then the exciting light is shone on a subject. An optical image of the subject illuminated by the exciting light is captured, whenever the field signal is alternately switched between high and low states, and then an image signal (referred to as IS1, IS2, IS3, IS4, IS5, and IS6 in the row "imaging device output" in FIG. 6) is sequentially generated.

When the fluorescence image observation mode is selected, the exciting-light control signal in the high state is sent to the image-processing unit 50 also. As described above, the image-processing unit 50 determines that image signals received from the AFE 33 every field period are fluorescence image signals. Accordingly, all the received fluorescence image signals are sent to the fluorescence-image processing circuit 52b via the first-signal processing circuit 51.

The fluorescence image signal is sent to the second image memory 53b and the second color gamma-correction circuit 54b from the fluorescence image processing circuit 52b, whenever the fluorescence image signal is received by the fluorescence-image processing circuit 52b. As described above, the fluorescence image signal (referred to as FS1, FS2, FS3, FS4, FS5, and FS6 in the row "second image memory" in FIG. 6) is stored in the second image memory 53b. In addition, the second color gamma-correction circuit 54b carries out color gamma correction on the received fluorescence image signal.

The fluorescence image signal (referred to as FS1, FS2, FS3, FS4, FS5, and FS6 in the row "image signal received by second-signal processing circuit" in FIG. 6) is sent to the second-signal processing circuit 55 from the second gamma correction circuit 54b. The second-signal processing circuit 55 receives an image signal only from the second color gamma-correction circuit 54b, and then, the second-signal processing circuit 55 generates a video signal based on the received fluorescence image signal without carrying out plural image display processing. There is displayed a fluorescence image (referred to as FS1, FS2, FS3, FS4, FS5, and FS6 in the row "displayed image" in FIG. 6) which is an optical image of a subject illuminated by the exciting light on the monitor 11.

Figure 7:
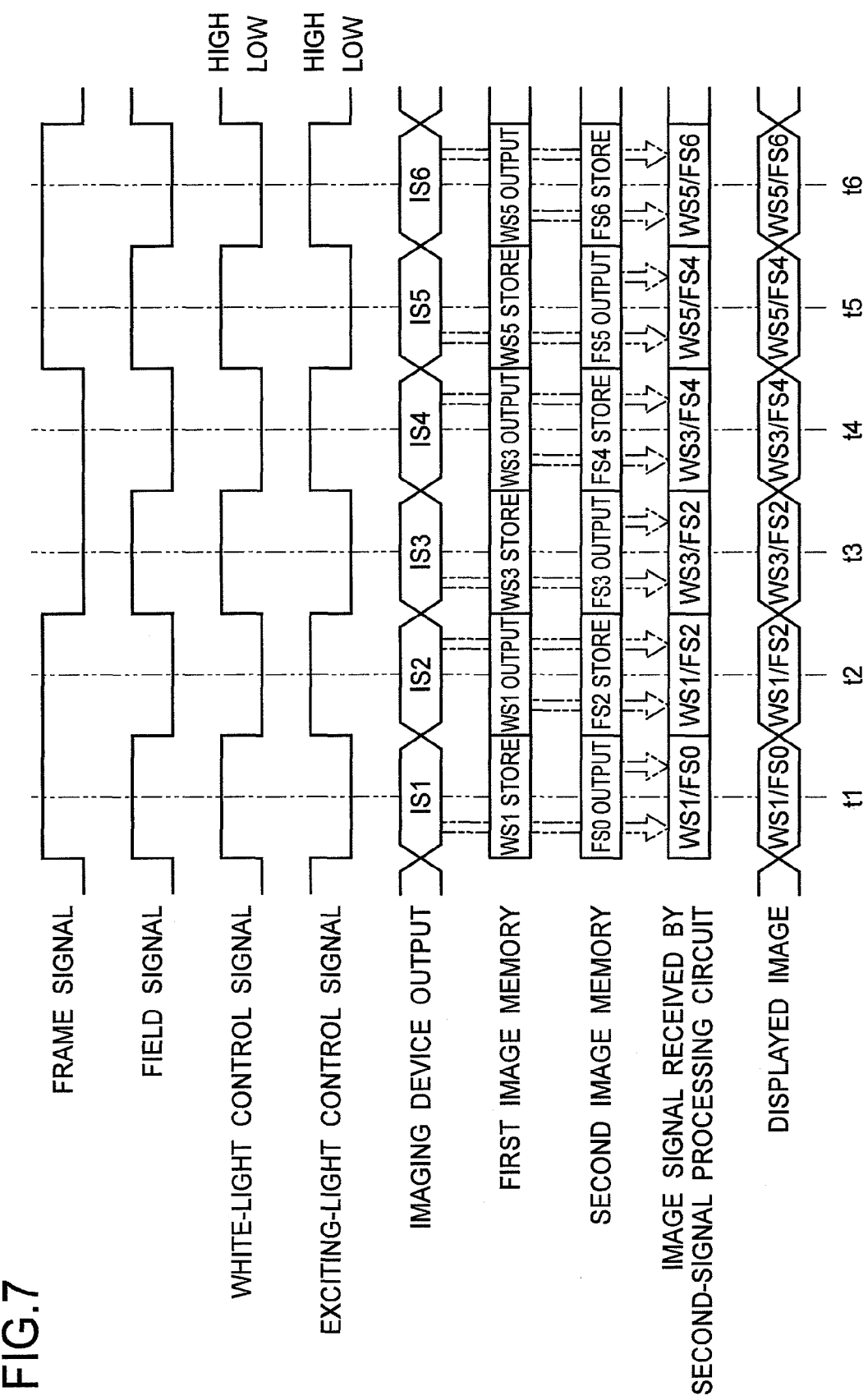
FIG. 7 is a timing chart illustrating the timing used to drive some components in the endoscope system in the two-image observation mode.

When the two-image observation mode is selected, the white-light control signal and the exciting-light control signal which are alternately switched between high and low states so as to synchronize the field signal, are sent to the shutter driver 47s and the exciting-light control circuit 46 from the timing controller 22, respectively (see the columns of "field signal", "white-light control signal", and "exciting-light control signal" in FIG. 7).

Accordingly, the light-source unit 40 alternately and repeatedly supplies the light guide with the white light and the exciting light synchronized with the field signal, and then the white light and the exciting light are alternately shone on a subject every field period. An optical image of the subject is captured, whenever the field signal is alternately switched between high and low states, and then an image signal (referred to as IS1, IS2, IS3, IS4, IS5, and IS6 in the row "imaging device output" in FIG. 7) is sequentially generated in each field period when the illumination light to the subject is altered.

When the two-image observation mode is selected, the white-light control signal and the exciting-light control signal which are alternately and repeatedly switched to the high state are sent to the image-processing unit 50 also. Accordingly, the image-processing unit 50 determines that the image signals (referred to as IS1, IS3, and IS5 in the row "imaging device output") received at the times t1, t3, and t5 when the white light is shone on the subject, are the white-light image signals. On the other hand, the image-processing unit 50 determines that the image signals (referred to as IS2, IS4, and IS6 in the row "imaging device output") received at the times t2, t4, and t6 when the exciting light is shone on the subject, are the fluorescence image signals.

As described above, the white-light image signals are sent to the white-light image-processing circuit 52a via the first-signal processing circuit 51. On the other hand, the fluorescence image signals are sent to the fluorescence-image processing circuit 52b via the first-signal processing circuit 51.

The determined white-light image signals, which are received by the white-light image-processing circuit 52a at the times t1, t3, and t5, are sent to and stored in the first image memory 53a (referred to as WS1, WS3, and WS5 in the row "first image memory"). Simultaneously, the determined white-light image signals are sent to the first color gamma-correction circuit 54a (referred to as WS1, WS3, and WS5 in the row "image signal received by second-signal processing circuit").

The determined fluorescence image signals, which are received by the fluorescence-image processing circuit 52b at the times t2, t4, and t6, are sent to and stored in the second image memory 53b (referred to as FS2, FS4, and FS6 in the row "second image memory"). Simultaneously, the determined fluorescence image signals are sent to the second color gamma-correction circuit 54b (referred to as FS2, FS4, and FS6 in the row "image signal received by second-signal processing circuit").

The white-light image signals stored in the first image memory 53a is read by the white-light image processing circuit 52a and sent to the first color gamma-correction circuit 54a in field periods (referred to as t2, t4, and t6) following the field periods during which they were stored in the first image memory 53a. The fluorescence image signals stored in the second image memory 53b is read by the fluorescence-image processing circuit 52b and sent to the second color gamma-correction circuit 54b in field periods (referred to as t3 and t5) following the field periods during which they were stored in the second image memory 53b.

Accordingly, the first color gamma-correction circuit 54a receives the same white-light image signal in successive two-field periods (referred to as t1 and t2, t3 and t4, t5 and t6), carries out color gamma correction, and sends it to the second-signal processing circuit 55. The second color gamma-correction circuit 54b receives the same fluorescence image signal in successive two-field periods (referred to as t2 and t3, t4 and t5), carries out color gamma correction, and sends it to the second-signal processing circuit 55.

The second-signal processing circuit 55 receives the white-light image signal and the fluorescence image signal from the first and second color gamma-correction circuits 54a and 54b, respectively, every field period. The second-signal processing circuit 55 carries out plural image display processing and generates the video signal based on the received white-light image signal and the received fluorescence image signal. Based on the video signal, a white-light image and a fluorescence image (see the row "displayed image") are displayed on the monitor 11.

In the above embodiment, as explained in detail below, adequate color gamma correction can be carried out on a white-light image signal and a fluorescence image signal when a white-light image and a fluorescence image should be simultaneously displayed on the monitor 11.

In comparing the frequency distributions of pixel signals which compose a white image signal to those of a fluorescence image signal, it is typical that a fluorescence image signal includes more pixel signals with low signal levels than a white image signal.

Accordingly, if the first gamma coefficient is used for color gamma-correction on a fluorescence image signal, it will overcorrect the colors at the low end of the signal level range, producing color noise in the fluorescence image.

In order to decrease color noise in the fluorescence image, a coefficient low enough for a fluorescence image signal in such a range, such as a second color gamma coefficient, should be used for color gamma correction. However, if the second color gamma coefficient is used for color gamma-correction on a white-light image signal, color might be faded at pixels with low luminance.

In a prior endoscope system, when a white-light image and a fluorescence image are simultaneously displayed, either a first color gamma coefficient or a second color gamma coefficient was used for color gamma correction on both a white-light image signal and a fluorescence image signal. Accordingly, one of two problems described above happened. On the other hand, in the above embodiment, color gamma-correction is carried out on the white-light image signal and the fluorescence image signal using the first and second color gamma coefficients, respectively. Accordingly, the above problems will not occur.

The endoscope processor 20 comprises the first and second image memories 53a and 53b in the above embodiment. However, the first and second image memories 53a and 53b may not be comprised. If the first and second image memories 53a and 53b are not comprised, the white-light image and the fluorescence image can not be simultaneously displayed. However, the white-light image and the fluorescence image can be individually displayed following adequate color gamma correction.

The first and second color gamma-correction circuits 54a and 54b carry out color gamma correction on the white-light image signal and the fluorescence image signal, in the above embodiment. However, a single color gamma-correction circuit may carry out color gamma-correction on the white-light image signal and the fluorescence image signal using the first and second color gamma coefficients, respectively.

For example, the same effect can be achieved by providing a coefficient memory for storing the first and second color gamma coefficients, and reading and using the first and second color gamma coefficients for color gamma correction if the single color gamma-correction circuit receives the white-light image signal and the fluorescence image signal, respectively.

The endoscope processor 20 may comprise a memory for storing the first and second color gamma coefficients so that the first and second color gamma-correction circuits 54a and 54b can read both of the first and second color gamma coefficients in the above embodiment. With such an endoscope processor, the processing speed of color gamma correction during illumination of a single kind of light to a subject, such as either of the white-light image observation mode and the fluorescence image observation mode, can be increased by alternately ordering the first and second color gamma-correction circuit 54a and 54b to carry out color gamma correction on image signals, which are sequentially generated every field period, using the same color gamma coefficient. For example, in the white-light image observation mode, the first and second color gamma-correction circuit 54a and 54b read the first color gamma coefficient, alternately receive white-light image signals sequentially generated by and sent from the imaging device 32, and alternately carry out color gamma correction on the received white-light image signal using the first color gamma coefficient.

The white light and the exciting light can be switched in the above embodiment. However, a kind of light which can be switched is not limited to the white light and the exciting light. As long as light of differing wavelength can be switched, adequate color gamma correction for each kind of image signal can be carried out as in the above embodiment.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2007-293113 (filed on Nov. 12, 2007), which is expressly incorporated herein, by reference, in its entirety.

The invention claimed is:

1. An endoscope processor, comprising:
a light source controller that can order first and second light sources to alternately emit first and second lights, respectively, the wavelength band of said first light differing from that of said second light;
an imaging device driver that orders an imaging device to generate first and second image signals by capturing an optical image of a subject while said first and said second lights are shone on said subject, respectively; and
a gamma-correction block that carries out gamma correction on said first and said second image signals using first and second color gamma coefficients, respectively, said first and said second color gamma coefficients being predetermined according to the wavelength band of said first and said second lights.

2. An endoscope processor according to claim 1, wherein said first light is white light and said second light is exciting light which makes tissue autofluoresce.

3. An endoscope processor according to claim 1, wherein said gamma-correction block comprises first and second correction blocks, said first and said second correction blocks carrying out gamma correction on said first and said second image signals using said first and said second color gamma coefficients, respectively.

4. An endoscope processor according to claim 1, further comprising a coefficient memory that stores said first and said second color gamma coefficients, said gamma-correction block carrying out gamma correction on said first image signal using said first color gamma coefficient stored in said coefficient memory when said gamma-correction block receives said first image signal, said gamma-correction block carrying out gamma correction on said second image signal using said second color gamma coefficient stored in said coefficient memory when said gamma-correction block receives said second image signal.

5. An endoscope processor according to claim 1, further comprising:

first and second image memories that store said first and said second image signals, respectively; and an image generation block that generates a third image signal and outputs said third image signal to a monitor, said third image signal corresponding to a third image including first and second images, said first and said second images corresponding to said first and said second image signals, respectively, said image generation block generating said third image signal based on said first image signal written in said first image memory and upon which said gamma-correction block has carried out gamma correction and said second image signal which said second image memory has stored and upon which said gamma-correction block has carried out gamma correction when said first image signal is written in said first image memory, said image generation block generating said third image signal based on said second image signal written in said second image memory and upon which said gamma-correction block has carried out gamma correction and said first image signal which said first image memory has stored and upon which said gamma-correction block has carried out gamma correction when said second image signal is written in said second image memory.

6. An endoscope processor according to claim 5, wherein, said first and said second image memory stores said first and said second image signals generated by said imaging device, respectively, said first and said second image signals being sent from said first and said second image memories to said gamma-correction block, respectively, and said gamma-correction block comprising first and second correction blocks, said first and said second correction blocks receiving said first and said second image signals, respectively, said first and said second correction blocks carrying out gamma correction on said first and said second image signals using said first and said second color gamma coefficients, respectively.

7. An endoscope processor according to claim 5, further comprising a coefficient memory that stores said first and said second color gamma coefficients, said gamma-correction block carrying out gamma correction on said first image signal using said first color gamma coefficient stored in said coefficient memory when said gamma-correction block receives said first image signal, said gamma-correction block carrying out gamma correction on said second image signal using said second color gamma coefficient stored in said coefficient memory when said gamma-correction block receives said second image signal, said first and said second image signals which said gamma-correction block carried out gamma correction on are stored in said first and said second image memories, respectively.

8. An endoscope system, comprising:

first and second light sources emit first and second lights, respectively, the wavelength band of said first light differing from that of said second light;

a light source controller that can order said first and said second light sources to alternately emit said first and said second lights, respectively;

a light guide that transmits said first and said second lights emitted by said first and said second light sources to a subject, respectively;

an endoscope that generates first and second image signals by capturing an optical image of said subject while said first and said second lights are shone on said subject, respectively; and a gamma-correction block that carries out gamma correction on said first and said second image signals using first and second color gamma coefficients, respectively, said first and said second color gamma coefficients predetermined according to the wavelength band of said first and said second lights.

* * * * *